United States Patent [19]
Hurtubise et al.

[11] Patent Number: 5,685,193
[45] Date of Patent: Nov. 11, 1997

[54] DISC BRAKE PAD ASSEMBLY PROOF-TESTING

[75] Inventors: Christopher James Hurtubise, Southfield, Mich.; Winston Randolph Mason, Jr.; James William Powe, both of Winchester, Va.

[73] Assignee: Cooper Industries, Inc., Houston, Tex.

[21] Appl. No.: 676,781

[22] Filed: Jul. 8, 1996

[51] Int. Cl.[6] .......................... G01B 21/08; G01N 17/00
[52] U.S. Cl. ........................ 73/150 A; 73/121; 73/830
[58] Field of Search .................. 73/150 A, 150 R, 73/818, 827, 830, 841, 842, 121, 132

[56] References Cited

U.S. PATENT DOCUMENTS

| | | | |
|---|---|---|---|
| 3,415,115 | 12/1968 | Newell | 73/121 |
| 3,634,930 | 1/1972 | Cranston | 73/830 |
| 3,782,185 | 1/1974 | Hassenauer et al. | 73/121 |
| 4,206,636 | 6/1980 | Hendrix | 73/132 |
| 4,393,699 | 7/1983 | Seiler, Jr. | 73/827 |
| 4,586,371 | 5/1986 | Ivie et al. | 73/827 |
| 5,176,028 | 1/1993 | Humphrey | 73/842 |

*Primary Examiner*—Richard Chilcot
*Assistant Examiner*—Max H. Noori
*Attorney, Agent, or Firm*—Thomas S. Baker, Jr.

[57] ABSTRACT

A method and apparatus for non-destructively proof-testing the integrity of the bond between an integrally-molded disc brake pad assembly metallic backing plate element and its adhered molded friction material pad element advantageously tests the bond by tensile stressing rather than by conventional shear stressing.

5 Claims, 2 Drawing Sheets

DISC BRAKE PAD ASSEMBLY PROOF-TESTING

CROSS-REFERENCE

None.

FIELD OF THE INVENTION

This invention relates generally to integrally-molded disc brake pad assemblies, and particularly concerns both a test method and a test apparatus which may be advantageously utilized for proving the integrity of the bond, developed during manufacture, between the backing plate component and the friction material component of an integrally-molded disc brake assembly.

BACKGROUND OF THE INVENTION

Heretofore it has been commonplace in different integrally-molded disc brake pad assembly manufacturing operations to test the integrity of the bond formed at the interface between the assembly backing plate and integrally-molded friction material components by subjecting the completed assembly to a destructive test procedure in which each bond tested is subjected to shear stresses along the plane of the bond until the bond fails. To effectively accomplish such shear stress testing it is necessary to first adequately secure the disc brake pad assembly backing plate component in a test fixture and then afterwards subject the assembly integrally-molded friction material component to a force or forces of predetermined magnitude which are applied to the cured friction material component in directions that are parallel to the plane of the backing plate component. If the bond being proof-tested is inadequate for intended assembly utilization, the predetermined force or forces will prematurely separate the integrally-molded friction material from the backing plate by bond shear failure. However, in accomplishing the conventional shear test the friction material previously extruded into the backing plate component extrusion openings is also subjected to shear in the plane of the bond and the shear resistances developed in that material can unduly mask the true strength of the bond condition being tested thereby resulting in a proof-testing result that is not indicative of the true bond strength.

We have discovered that the reliability shortcomings of the conventional proof-test procedure can be overcome, and that the proof-testing operation also can be simplified to a single-step non-destructive operation by using test forces which are oriented in a substantially different direction than the conventional shear stress-inducing forces previously utilized. In carrying out our novel method of proof-testing integrally-molded disc brake pad assemblies we subject the assembly bonds to potential failures using test forces which are applied to the assembly friction material components in directions that are basically normal to the plane of each disc brake pad assembly backing plate component and which induce bond test failure, if present, in a tensile stress mode rather than a shear stress mode. Also, and if optionally desired, the novel disc brake pad assembly bond tensile-testing operation may further include a simultaneous operation of impression-marking the assembly metallic backing plate component with identifying information such as manufacturer's name or logo, manufacturer's part number, manufacturing lot number, and the like.

Other objectives and advantages of the present invention will become apparent from consideration of the additional invention details which follow.

SUMMARY OF THE INVENTION

The integrally-molded disc brake pad assembly to which the present invention has application typically consists of a conventional metallic backing plate component having one or more interiorly-located extrusion openings and of a friction material pad component that is both bonded to the mating surface of the backing plate component during forming and thermal curing of the friction material and additionally in-part extruded into the backing plate component extrusion openings.

To non-destructively proof-test a particular, so-constructed disc brake pad assembly we provide a work station having a support surface which supports the assembly backing plate component and also having an overly-deep cavity which is in the support surface and which receives the assembly integrally-molded pad component. In addition, we provided the work station with a novel assembly hold-down or clamping bar having proof-load pin elements that, during the clamping step of the test operation, co-operate with and apply compressive forces to the friction material located in the backing plate component extrusion openings of the disc brake pad assembly being tested. The apparatus hold-down bar pin elements are oriented perpendicular to the upper face of the pad assembly metallic backing plate component and, when the clamping bar is actuated, are brought into contact with the pad assembly by means of a connected selectively operated hydraulic or pneumatic actuator. The proof-load pin elements are spring-loaded and, because of the restraint of the backing plate component, subject the principal bonded interface between the assembly backing plate and friction material pad components to tension stresses. If the bonded interface is defective and therefore unsuited to the intended brake pad assembly application, the friction material pad component is separated from the backing plate component to thus reveal the bond deficiency. If the bonded interface is sound the brake pad assembly remains intact and may be utilized in a brake assembly.

The test apparatus is further preferably provided with an ejector sub-assembly which functions to remove the tested assembly, or its separated component parts (in the case of a deficient interface bond) from being within the work station cavity on completion of the assembly proof testing operation. Also, the work station test apparatus may optionally be combined with a separate and selectively-operable sub-assembly for applying manufacturer's logo, manufacturer's part number, and manufacturing lot number information to the brake pad assembly backing plate component by impression stamping.

Additional details regarding the present invention are provided in the drawings, detailed specification, and claims which follow.

DETAILED DESCRIPTION

Figure 1:
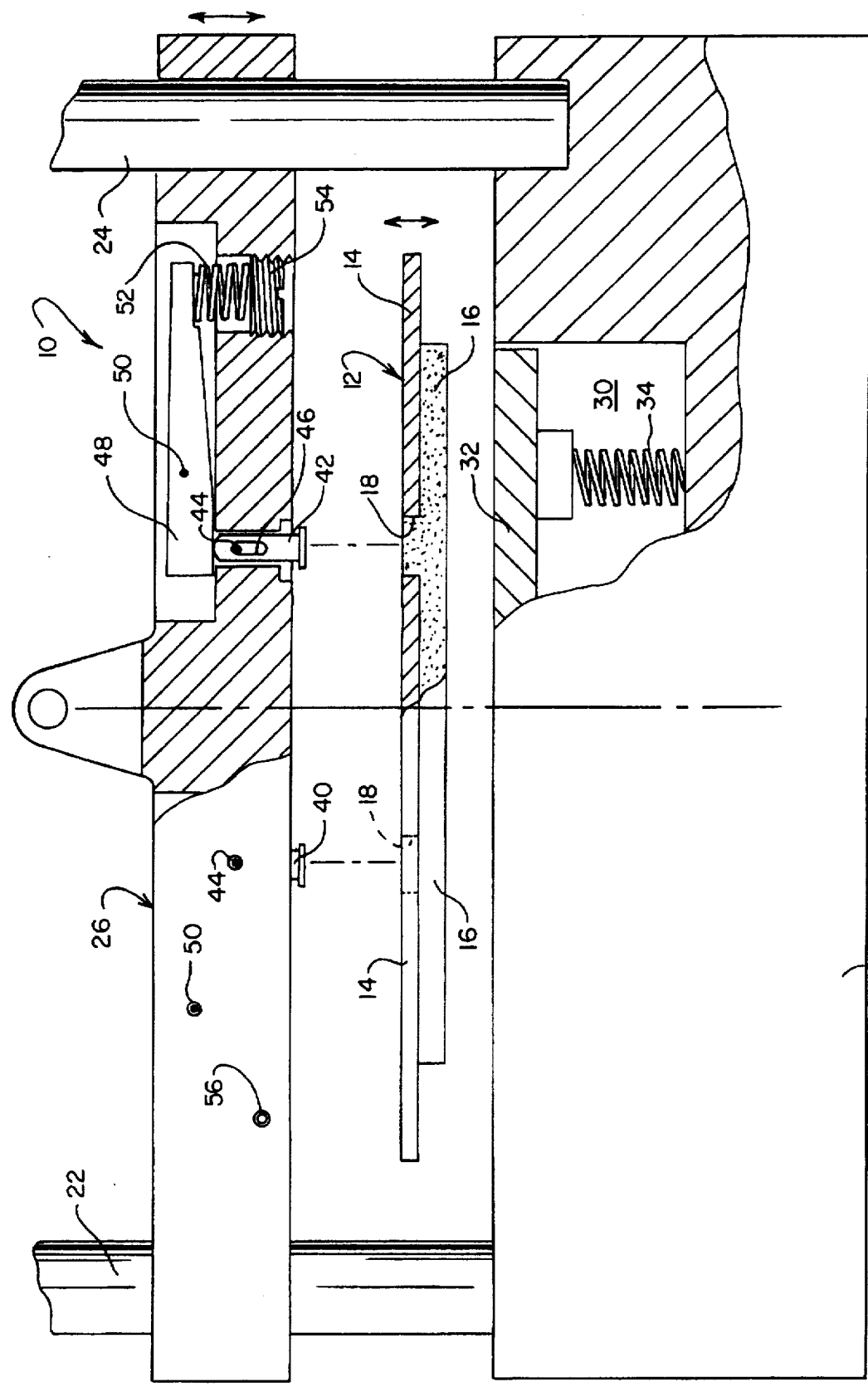
FIG. 1 is a schematic and partially-sectioned elevation view of a preferred embodiment of the test apparatus of the present invention illustrated in an open or un-clamped condition as for inserting or removing a disc brake pad assembly before or after proof-testing.

In FIG. 1 we schematically illustrate part of a non-destructive proof-test apparatus 10 that we prefer for use in proof-testing a disk brake pad assembly such as assembly 12 to determine by tension-testing rather than shear-testing whether the bond formed between the assembly backing plate element 14 and the assembly integrally-molded friction material element 16 is sufficient to permit the ultimate use of assembly 12 in its intended vehicular braking system application. Backing plate element 14 is typically provided with two or more interiorly-located plate openings 18 into which particulate friction material combined with a thermosetting adhesive resin is extruded and cured during the manufacturing step of forming integrally-adhered friction material element 16.

Figure 2:
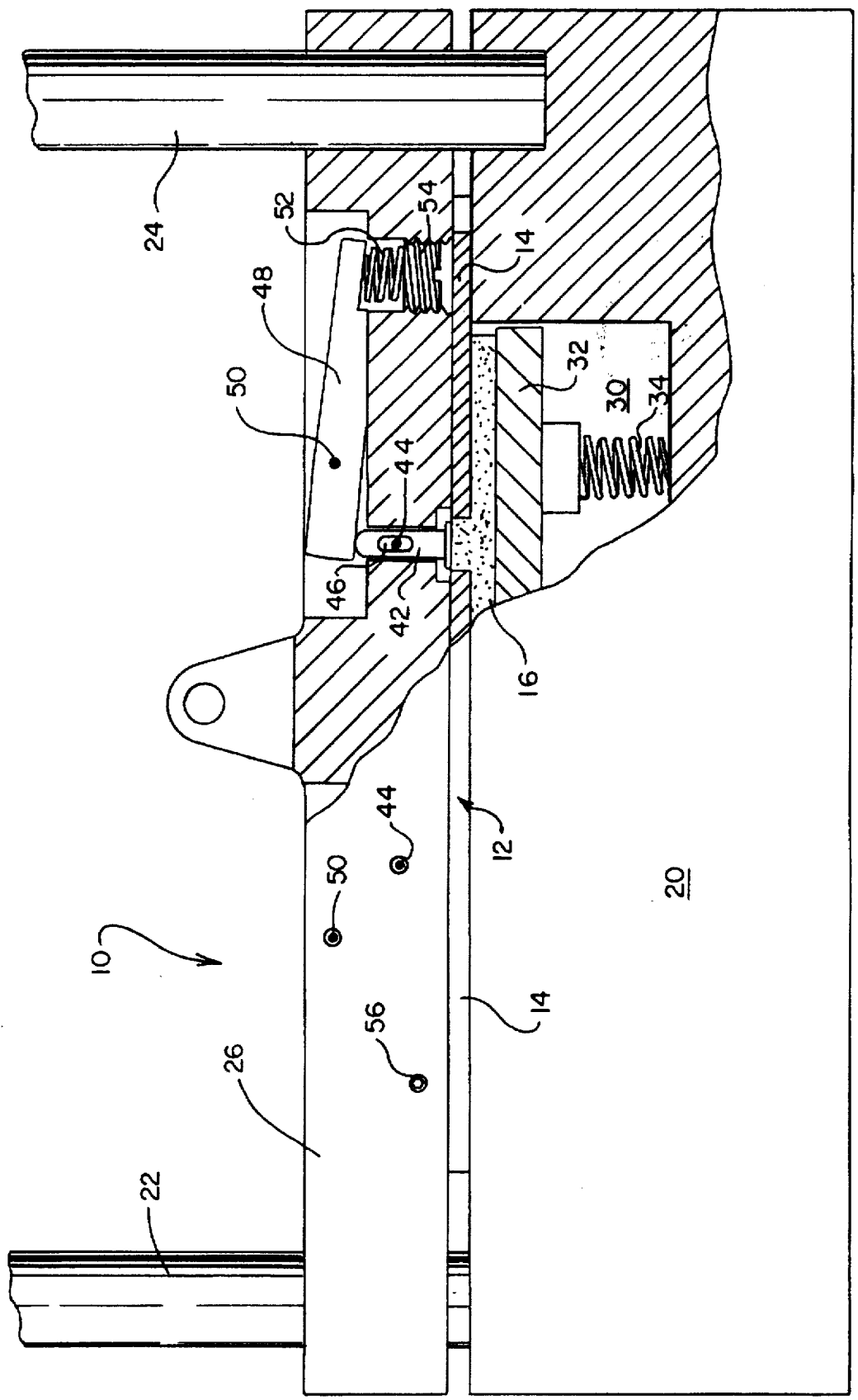
FIG. 2 is a view similar to FIG. 1 but illustrating the test apparatus of the present invention in a closed or fully-clamped condition at the culmination of the preferred proof-testing operation but prior to removal of the proof-tested disc brake pad assembly.

Apparatus assembly 10 is basically comprised of a base element 20, of a pair of cylindrical guide columns 22 and 24 mounted in the base element, and of a hold-down bar element 26 which co-operates with and is guided in its vertical movement by columns 22 and 24. Not shown in the drawings are a conventional apparatus cross-head element that is connected to and supported by the upper extremes of columns 22 and 24. Also not illustrated in the drawings is the apparatus conventional extendable and retractable hydraulic or pneumatic actuator element that is connected to both the cross-head element and to a clevis feature of hold-down bar element 26, and that may be selectively actuated in opposite directions to move element 26 to and from a position of clamping engagement with the disk brake pad assembly being proof-tested. FIG. 1 illustrates element 26 in a non-clamping condition relative to assembly 12, whereas FIG. 2 illustrates element 26 and assembly 12 in a fully-clamped condition.

Apparatus base 20 includes a cavity 30 in which is installed a vertically-yieldable ejector platform 32 that is supported by spring elements such as compression spring 34 such that its upper surface is flush with the upper surface of base element 20 when supporting only the weight of a properly-positioned and co-operating disk brake pad assembly 12. Also, the spring elements 34 included in apparatus 10 are selected so that a minimal total force approximately equal to the weight of the assembly being tested is required to cause their compression over a distance equal to the total thickness of assembly 12 when assembly 12 is subsequently positioned in apparatus 10 a fully-clamped condition.

Referring to FIG. 1, vertically movable hold-down bar element 26 is provided with a pair of proof-load pin elements 40 and 42 that are each aligned with a respective one of the extrusion openings 18 incorporated in the backing plate element of the disc brake pad assembly to be tested. Each such pin element is vertically movable relative to the body of element 26 over a limited distance determined by co-operating pin dowel element 44 and the length of co-operating pin slot element 46. Also, each such pin projects below the under surface of hold-down bar element 26 a short distance when apparatus 10 is actuated to an open or disc brake pad assembly-receiving condition.

Also provided in hold-down bar element 26 in a recess is a rocker element 48 pivotally supported by rocker pin element 50, a heavy-duty compression or die spring 52 which is restrained from downward movement by threaded adjustment screw element 54 and which is compressed by rocker element 48 whenever a respective proof-load pin element 40 or 42 is moved vertically upward as a consequence of downward clamping action of hold-down bar element 26 and the developed strength of the bond of assembly 12 being tested. A conventional set screw device such as 56 may be included in hold-down bar element 26 for the purpose of locking adjustment screw element 54 in position after a proper degree of initial compression has been incorporated into compression spring element FIG. 2 illustrates the same component parts as are illustrated in FIG. 1 but with the apparatus 10 actuated to a closed or full-clamping condition. In that condition the disc brake pad assembly backing plate element 14 is supported by the upper surface of the apparatus base 20. If the bond between that assembly element and integrally-molded friction material 16 has a tensile strength below an acceptable level, the resulting test forces developed by the downward movement of hold-down bar element 26 and the compression of spring elements 52, as transmitted through the arms of rocker elements 48 and the respective co-operating proof-load pin element 40 or 42, all or portions of molded friction material 16 will be separated from backing plate element 14 and will remain on ejector plate 32 when the proof-tested assembly 12 is removed from apparatus 10 thus indicating that an unsatisfactory bond was developed in the assembly 12 manufacturing process.

We have determined by experience that a total compression force developed in proof-load pin elements 40 and 42 by compressing spring elements 52 and by the full clamping action of hold-down bar element 26 may be as small as approximately twenty percent (20%) of the total force of bond resistance to tension separation from backing plate element 14 in areas surrounding extrusion opening 18 and any consequent non-failure of the tested assembly bond will satisfactorily predict that the tested disc brake pad assembly 12 is suitable for incorporation into its intended automotive vehicle disc brake braking system application.

We claim as our invention:

1. In a method of proof testing the bond integrity of an integrally-molded disc brake pad assembly having a metallic backing plate element provided with at least one interior extrusion opening and having a molded friction material pad element bonded to said backing plate element and extruded into the backing plate element extrusion opening, the steps of:

restraining said assembly metallic backing plate element against movement along a first direction;

positioning a rigid proof-load pin test element in non-adhered contact with said molded friction material pad element at said backing plate element extrusion opening;

applying a compressive force to said rigid proof-load pin test element and to said molded friction material pad element at said metallic backing plate element interior extrusion opening in a direction substantially parallel to said first direction; and removing said rigid proof-load pin test element from contacting relation with said molded friction material pad element, said applied compressive force subjecting portions of the bond of said molded friction material pad element to said metallic backing plate in areas adjacent said metallic backing plate element extrusion opening to potential failure by tensile stressing without separating portions of said molded friction material pad element from said metallic backing plate element.

2. The method defined by claim 1 wherein said applied compressive force has a magnitude that is at least approximately twenty percent (20%) of the magnitude of the total tension force bonding said molded friction material pad element to said metallic backing plate element in areas adjacent said metallic backing plate element extrusion opening.

3. The method defined by claim 1 wherein said applied compressive force is oriented in a direction substantially at right angles to the orientation of the principal longitudinal direction of said metallic backing plate element.

4. The method defined by claim 1 wherein said applied compressive stress has a variable magnitude determined by the degree of compression of a spring.

5. In test apparatus for use in proof-testing a disc brake pad assembly having a metallic backing plate element provided with at least one interior extrusion opening and having an integrally-molded friction material pad element bonded to said metallic backing plate element and extruded into said metallic backing plate element interior extrusion opening, in combination:

base means supporting said metallic backing plate element against movement in a downward direction and receiving said integrally-molded friction material pad element in an internal cavity;

a vertically movable hold-down bar element having an interior proof-load pin element vertically aligned with said metallic backing plate element interior extrusion opening; and compression spring means co-operating with said hold-down bar proof-load pin element and variably pressing said proof-load pin element into direct contact with said integrally-molded friction material pad element when said hold-down bar element is brought into engagement with said metallic backing plate element, said compression spring means simultaneously placing the integral bond between said molded friction material pad element and said metallic backing plate element in tension in regions surrounding said metallic backing plate element extrusion opening when said hold-down bar element contacts said metallic backing plate element in clamping relation to said base means and compresses said compression spring means.

* * * * *